United States Patent [19]

Bonham

[11] Patent Number: 5,040,888

[45] Date of Patent: Aug. 20, 1991

[54] HOLOGRAM SYSTEM WHICH HELPS REDUCE EYE STRAIN

[76] Inventor: Celeste V. Bonham, P.O. Box 1677, Topanga, Calif. 90290

[21] Appl. No.: 537,110

[22] Filed: Jun. 13, 1990

Related U.S. Application Data

[63] Continuation-in-part of Ser. No. 375,834, Jul. 5, 1989, Pat. No. 4,950,067.

[51] Int. Cl.[5] .......................... A61B 3/00; G03H 1/02

[52] U.S. Cl. .................................... 351/203; 351/246; 359/1

[58] Field of Search .................. 350/3.6, 3.7; 351/201, 351/203, 206, 246; 128/25 A

[56] References Cited

U.S. PATENT DOCUMENTS 4,376,950 3/1983 Brown et al. ........................ 350/3.6

4,950,067 8/1990 Bonham ............................. 351/203

*Primary Examiner*—Paul M. Dzierzynski

[57] ABSTRACT

A holographic system which contains a multiple image hologram comprised of two or more images at varying focal distances, which when viewed consecutively and in repetition will exercise the ciliary muscle of the eyes. The holographic system will have its own power to illuminate said hologram. The shifting of conditions of the viewer to alternate the viewing of one image and then the other, may involve the physical movement of the user's head, or the system may contain a motor coupled to rotate said system. The system may include a clock-timer to activate said motor, and for periodically illuminating the hologram. The system may include a sound alarm to remind the viewer to utilize the holographic system.

12 Claims, 1 Drawing Sheet

Fig. 1.
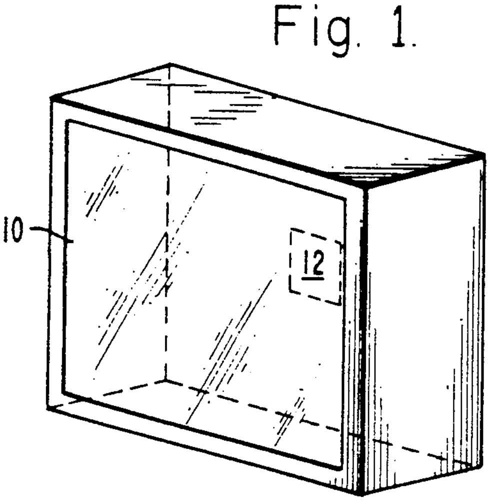
Fig. 2.
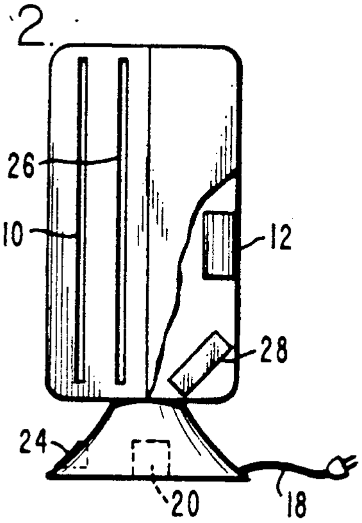
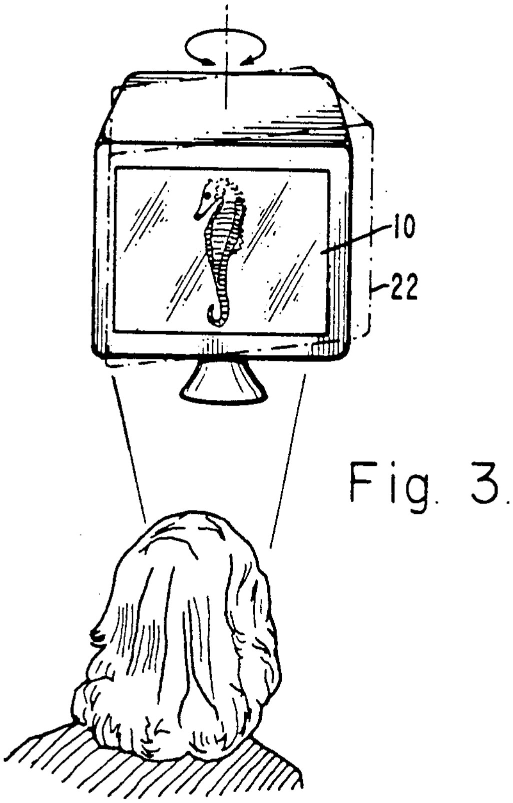
Fig. 3.
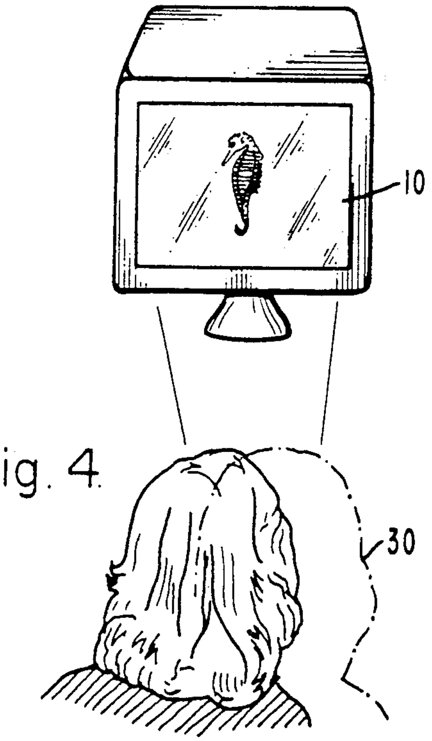
Fig. 4.
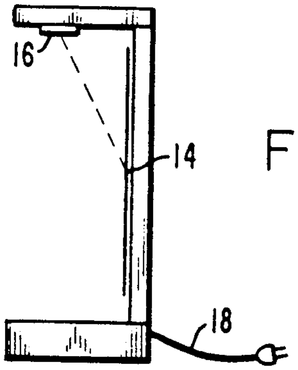
Fig. 5.

HOLOGRAM SYSTEM WHICH HELPS REDUCE EYE STRAIN

RELATED PATENT APPLICATION

This patent application is a continuation-in-part of my U.S. patent application Ser. No. 07/375,834, Filed July 5, 1989, now U.S. Pat. No. 4,950,067 entitled HOLOGRAM WHICH HELPS REDUCE EYE STRAIN.

BACKGROUND-FIELD OF INVENTION

This invention relates to eye exercising by changing focal distances and points which will help to reduce eye strain; specifically utilizing three-dimensional opticals in a hologram.

BACKGROUND-DISCUSSION OF PRIOR ART

We live in a computer age where computers are becoming more incorporated into our society with every passing year. Our future will become more computerized as technology broadens and the ease for the user is simplified.

This vast growing industry has lead to a very dangerous medical problem: Weakening of the eyes due to extended viewing of VDTs (video-display terminals). Any work that requires continuous close viewing over long periods of time without exercising and "stretching" the eye ciliary muscles can lead to eye strain. This problem is not limited only to the VDT user but can include persons who read extensively, watch television for long periods of time, and anyone whose daily life encompasses extended close viewing over long periods of time. To properly exercise and stretch the ciliary muscle of the eye one must shift focus from distances far to near and back again.

I experienced the difficulty in focusing of vision after extended use on my computer. An eye doctor informed me to take breaks in my work schedule and exercise my eyes. He suggested that I focus on my thumb and then on the corner in the room not closer than a distance of six feet. From an eyesight standpoint, 20 feet is comparable to infinity. Doing this exercise every 15 to 30 minutes for about 10 to 15 seconds would largely reduce the eye strain I was experiencing. I researched in the library editorial section and found a vast array of articles written in such major publications as: U.S. News & World Report, Forbes, Scientific American, PC-Personal Computing, PC Week, etc. Each of these articles noted the growing problem of eye strain in the work place and especially where computers are being used. In May 1989, OSHA released a study on VDT user problems titled, Ad Hoc Expert Advisory Committee On Visual Display Terminals. In this report it states the leading negative effect on the user is the difficulty of focusing after extended use on the VDT. Some articles also stated that the increasingly high percentage of children having to wear glasses at an earlier age than in the past is directly related to eye strain. Research has concluded that children are becoming more indoctrinated and educated on computers as technology advances. With the growing attraction to television, children are not getting enough eye exercise needed to keep the eyes healthy, thus resulting in early eye impairment and the need of eye glasses. We cannot change man's evolution and the advancement of technology, but with the correct use of this simple invention it can help to avoid the eye impairment caused by improperly using the eyes. I have not found an invention in the marketplace which directly aids in this problem. Presently eye doctors are using 3-D glasses for therapy designed with images to focus upon. The problem with such an eye exercise device as these glasses is that when worn they totally preclude the viewer from seeing anything but that which is photographed inside the glasses. One has to stop all work when wearing these glasses. Searching through the patent library I found no prior art or patents of devices or systems to help strengthen the eye muscles through 3-D holographic opticals recorded at different focal points and distances. I searched through U.S. Patent Office Class 350 (Optics Systems & Elements) 3.7 (Using a hologram as an ordinary optical element) and 3.84 (Focused image holography); and through Class 351 (Optics - Eye examining, Vision, Testing & Correcting) 203 (Eye exercising or training type) to no avail. None of the prior art or patents directly utilized holograms to strengthen the eye muscles by changing focal points by using various opticals contained within the hologram itself.

With reference to Brown et al. (4,376,950) which was brought to my attention by the patent examiner, I see no conflict or infringement of patent rights since Brown et al. does not claim to be a device for exercising the eyes. My invention has a specific function of eye exercising by changing focus length when providing two or more images appearing at different focus distances. The purpose of my invention is exclusive to exercising the eyes. Brown suggests the need of an exterior lens 28 as noted in FIG. 1. My invention does not need any lens assistance to view the 3-D holographic images.

SUMMARY OF THE INVENTION

In accordance with my invention, an image multiplexing hologram is provided, with one image appearing to be very close to the viewer, and at least one other image appearing to be at a substantial distance from the viewer at a remote point. A stand mounting may be provided for convenience of the user; and suitable illuminating arrangements provided.

Supplemental features could include a motor for moving the hologram, an electrical power circuit and/or battery compartment, and a clock/timer for periodically turning the illumination and/or motor on and off.

The system includes its own light source to illuminate the opticals, thereby giving stronger and more distinctive images to focus upon.

OBJECTS AND ADVANTAGES

Accordingly, there are several objects and advantages to my invention, and certain of these objects are:

(a) to provide an exercise for the eye muscles which helps to reduce eye strain;

(b) to provide an easily accessible invention for consumers which will help strengthen their eyesight;

(c) to provide an entertaining visual display which will attract the attention of the consumer causing its extended and continued use;

(d) to provide an alternative relaxed visual which will also incorporate peace of mind and help reduce stress connected with the extended use of VDTs, books, or television;

(e) to provide less stress of the eyes which will reduce headaches and job absenteeism;

(f) in addition, holograms will be designed for individual age groups, thereby attracting its use to a broader age range from young children to adults.

Further advantages will become apparent from a consideration of the following description and the accompanying drawings.

BRIEF DESCRIPTION OF DRAWINGS

FIG. 1 is a perspective view of a holographic system illustrating the invention when a transmission hologram is used;

FIG. 2 is the side view of my invention showing the hologram, the light system, a backing board, a clock and/or timer, an electrical source, mirror(s) to reflect light, and a motor which could cause the box itself to move the appropriate distance to change the holographic images in my invention for the viewer;

FIG. 3 and FIG. 4 are perspective views each illustrating an embodiment of my invention when used by a viewer. These FIGS. 3 and 4 illustrate the image changing in the hologram with a slight movement of the head, or the movement of the light box itself, respectively; and FIG. 5 is a side view of the holographic system wherein a reflective hologram is used; thereby requiring a light source to illuminate the hologram from a frontal position.

DETAILED DESCRIPTION OF PREFERRED EMBODIMENTS

A hologram is a medium which enables the storage of three-dimensional visual information on a two-dimensional plane. A hologram is not a new invention. It was first invented in 1947 by Dr. Dennis Gabor and has been successfully improved over the years.

The image multiplexing opticals within the hologram will be recorded with a laser light on an unexposed emulsion (glass or film) while facing a three-dimensional object. The Image Multiplexing chapter in the book, HOLOGRAPHY, Expanded and Revised from the French Edition, by M. Francon, fully details and explains the image multiplexing process for holography. The laser, emitting a beam of pure coherent light, is optically split into two beams on a complex optical vibration isolation table. One beam is used to illuminate the real three-dimensional object which reflects its light properties onto the emulsion, while the other beam is directed straight at the emulsion. The film receives the patterns of both the object's reflected light (the object beam) and the direct laser light (the reference beam) resulting in an interference pattern recording where the beams intersect on the unexposed emulsion.

To acquire the image multiplexing within the hologram, the signal (object) to be recorded is placed adjacent to a diffuser which is illuminated by a laser. Between the signal and the photographic plate is a diaphragm with an aperture which will be formed from more than one sector. The plate is illuminated by a reference beam to record a hologram as previously described in preceeding paragraph. After the first exposure, the signal is replaced by a different signal and a second exposure is made with the sectors rotated to occupy another position or "window" on the plate which does not overlap the first. By using an actual diaphragm to isolate one of the images in a given window, we reconstruct only that signal to which it corresponds. Several exposures are made each having their own window with the signal to be recorded and the position of the sectors changed each time.

The film is then developed recording the information of the object and its light patterns. After development, the hologram is placed precisely in its initial position and each window is illuminated by a reference wave. The hologram is illuminated either with a laser or incandescent light source positioned at the exact angle of the original reference beam recording. The interference pattern is then activated, causing the recording of the original object in each window to appear in the hologram exactly as it originally was, suspended in space, in all its total dimension. In my holographic system there will be two or more three-dimensional opticals at various focal distances contained in the hologram. Each recording will be illuminated by positioning the light source at the exact angle of the original reference beam recording. To change the position of the reference beam onto another window of the hologram and illuminate the object, a slight movement of the head or the movement of the system itself will cause the images in the hologram to change.

The size of the hologram will vary depending on the dimensions of the hologram support and illumination. There is no limitation to the size or the shape (square, circle, rectangular, etc.) of the hologram. The hologram can be displayed in a free standing, self-contained display, and may include its own light source, clock, timer, or motorized device which will move or rotate the display box by the appropriate distance or angle to change the images viewed in the hologram.

This invention can be either a transmission hologram (FIG. 1) or a reflective hologram (FIG. 5). The difference of these are determined by the placement of the light source configuration and the type of hologram which is used. In a transmission hologram (FIG. 1) the viewing light source 12 will apply illumination through the hologram 10, which is between the viewer and the light source 12. For a reflective hologram (FIG. 5), the hologram 14 will be illuminated by the reflection of an exterior light 16 positioned at the appropriate angle in front of the hologram 14. In both the transmission and reflective holograms the light source 12,16 will be powered by means of an electrical source 18 or batteries. The side illustration (FIG. 2.) of a transmission system shows the hologram 10, and the motor 20 which can cause the display box to pivot to the position indicated at reference numeral 22 as shown in FIG. 3. FIG. 2 also shows the light source 12, electrical power source 18, clock/timer 24 which can be programmed to periodically activate the light source 12 and the motor 20, a backing board 26 behind the hologram to block extraneous objects from the viewed holographic images, and a mirror 28 to reflect the light thus allowing the light from the light source 12 to travel to the holographic image 10, in a manner known in the holographic field.

FIG. 3 and FIG. 4 demonstrate the practical use of the system. FIG. 3 demonstrates the holographic image 10 changing due to the slight movement of the system 22, as the hologram 10 is rotated by motor 20. FIG. 4 demonstrates the holographic image 10 changing by the slight movement of the head as indicated by reference numeral 30. In FIGS. 3 and 4, examples are given showing a seahorse image which appears to be close to the viewer in FIG. 3, and one which appears to be remote from the viewer in FIG. 4. In practice, the two or more images would be contained in one hologram, and would be changed by relative movement of the hologram and the viewer, either as shown in FIG. 3 or in FIG. 4.

My invention can have a wide array of optical visuals - the images are limitless with the only prerequisite that there is a change of focal distances within the two or more opticals contained within the hologram.

OPERATION OF INVENTION

The manner of using the hologram system is quite simple. First of all activate the light source 12 to illuminate the opticals contained in the film of the hologram 10. The light source 12 can be illuminated at all times or can be controlled by a switch, button, voice activated or preprogrammed with a timer and/or clock 24. Focus on one of the images in the hologram. Once you have a strong focus on this image displayed in the hologram, slightly move your body 30 to change the position of your head and eyes FIG. 4, or if the box is motorized 20 it will automatically change the position of the box 22 in FIG. 3., and another image at a different focal point will be illuminated. Focus on this new image in the hologram. Once you have a strong focus of this image, slightly change the position of your head and eyes 30, or the box will automatically return to the first position 22, and you will return to your first image. If the hologram is designed with more than two images, then with the different positions of the body and the box each image within the hologram will have its position of illumination. The images will be designed to give the viewer images with various focal points. To properly exercise the ciliary muscle, focus on each image for not less than ten to fifteen seconds every fifteen to thirty minutes and this exercise will help strengthen and stretch your ciliary eye muscles thus helping to reduce eye strain. The clock/timer 24 is provided with an alarm which may be selectively turned on to alert the user to view the system of the present invention at intervals as noted above.

Conclusion and Ramifications

Thus the reader will see that this invention provides a very simple solution to a vast growing problem of eye strain by exercising the ciliary eye muscles. This problem has been greatly acknowledged and emphasized within the computer age we live in. The simplicity of the invention allows for this to be a very reasonable and economical device. Furthermore, it has the additional advantages in that:

- it is not limited to one age group but allows children as well as adults to benefit from its use;
- it is economically accessible to the consumer;
- with entertaining, interesting, and relaxing optics, the viewer will be more apt to want to use the invention, whereby the more one uses the invention, the more the ciliary muscle is exercised.

While my above description contains specifications, these should not be construed as limitations on the scope of the invention, but rather as an exemplification of preferred embodiments thereof. Many other variations are possible. For example: FIG. 1 and FIG. 5 shows existing types of display units. In an alternative display, the holographic invention could be attached to the computer monitor casing. Ultimately, I see this invention being incorporated within a software program so that with a touch of a finger the hologram images will appear on the screen of the monitor whereby the user may have easy access to the use of the invention.

Accordingly, the scope of the invention should be determined not by the embodiment illustrated, but by the appended claims and their legal equivalents.

I claim:

1. A method of stimulating the eye muscles with an optical system including a hologram, having multiple images appearing to be located at significantly different distances from the viewer, one image appearing to be very close to the viewer and one image substantially at an infinite distance from the viewer, comprising the steps of:

(a) mounting the optical system including the hologram in a light box casement on a stand;

(b) illuminating the optical images;

(c) having a viewer strongly focus on one of the images of the optical system appearing to be at one distance form the viewer;

(d) shifting the optical conditions to present to the viewer another of the images of the optical system appearing to be at a different distance from the viewer and having the viewer strongly focus on this different image, thereby exercising the viewer's eye muscles; and (e) operating a video display terminal for periodic intervals, and then interrupting the operation of the video display terminal and performing steps (a) and (d) as set forth hereinabove for an interval of time before resuming operation of the terminal.

2. A method as defined in claim 1 wherein the illumination of the optical image is periodically activated by a clock/timer.

3. A method as defined in claim 1 wherein a clock-/timer periodically sounds an alarm to alert the viewer to use the optical system.

4. A method as defined in claim 1 wherein said system includes a motor coupled to rotate the light box casement holding the hologram thus shifting the relative position of the user's head and that of the hologram.

5. A method as defined in claim 4 wherein a timer/-clock is provided to activate said motor.

6. A system for stimulating and exercising the eye muscles comprising:

a hologram having multiple images appearing to be located at significantly different distances from the viewer, one very close to the viewer and one at an infinite distance from the viewer;

means for mounting said hologram on a stand;

means for illuminating said hologram;

means for permitting shifting conditions for the user to alternate viewing one image and then the other;

a motor coupled to rotate the hologram; and a clock/timer means for periodically operating the illuminating means and/or the motor.

7. A system as defined in claim 6 wherein said system includes a sound alarm activated by clock/timer to remind the viewer to utilize the display.

8. A system as defined in claim 6 including mirror means for directing illumination onto the hologram.

9. A method of stimulating the eye muscles with a hologram having multiple images appearing to be located at significantly different distances from the viewer, one image appearing to be very close to the viewer and one image substantially at an infinite distance from the viewer, comprising the steps of:

mounting the hologram in a light box casement on a stand; p1 illuminating the hologram;

having a viewer strongly focus on one of the images of the hologram appearing to be at one distance from the viewer;

shifting the relative position of the viewer's head and the hologram by moving the light box casement to present to the viewer another image of the hologram appearing to be at a different distance from the viewer and having the viewer strongly focus on this different image, thereby exercising the viewer's eye muscles;

providing a motor coupled to rotate said light box casement housing the hologram, and activating said motor by a clock timer.

10. A method as defined in claim 9 for including a clock/timer to activate the periodically illumination of the hologram.

11. A method as defined in claim 9 including a clock-timer including a sound alarm to remind the viewer to utilize the hologram system.

12. A method as defined in claim 9 wherein the motor is activated by a clock-timer.

* * * * *